United States Patent [19]

Hirose et al.

[11] Patent Number: 5,663,376
[45] Date of Patent: Sep. 2, 1997

[54] PROCESS FOR THE PREPARATION OF α-TOCOPHEROL

[75] Inventors: Noriyasu Hirose, Tokyo; Hiroshi Inoue, Gifu Prefecture; Toshio Matsunami, Gifu Prefecture; Takashi Yoshimura, Gifu Prefecture; Kouzou Morita, Aichi Prefecture; Yuh Horikawa; Noriyoshi Iwata, both of Gifu Prefecture; Norio Minami; Kenji Hayashi, both of Ibaraki Prefecture; Chiaki Seki, Aichi Prefecture, all of Japan

[73] Assignee: Eisai Co., Ltd., Tokyo, Japan

[21] Appl. No.: 460,667

[22] Filed: Jun. 2, 1995

[30] Foreign Application Priority Data

Jul. 27, 1994 [JP] Japan ................................. 6-175167
Nov. 16, 1994 [JP] Japan ................................. 6-282309

[51] Int. Cl.$^6$ ................................................ C07D 311/72
[52] U.S. Cl. ........................................................ 549/411
[58] Field of Search ................................................ 549/411

[56] References Cited

U.S. PATENT DOCUMENTS 4,168,271  9/1979  Cardenas et al. ........................ 549/411

*Primary Examiner*—Nicky Chan
*Attorney, Agent, or Firm*—Wenderoth, Lind & Ponack

[57] ABSTRACT

A process is provided for the preparation of α-tocopherol. According to the process, a condensation reaction between trimethylhydroquinone and a specific phytol derivative or isophytol is conducted in the presence of any one of the following solvents:

(i) a carbonate ester, (ii) a lower fatty acid ester represented by the following formula:

$$R^1COOR^2$$

wherein $R^1$ means a lower alkyl group having 1–4 carbon atoms and $R^2$ means a lower alkyl group having 1–5 carbon atoms with the proviso that methyl acetate and ethyl acetate are excluded;

(iii) a mixed solvent of a nonpolar solvent and a lower alcohol having 1–5 carbon atoms; and (iv) a mixed solvent of the nonpolar solvent and the lower fatty acid ester.

2 Claims, No Drawings

PROCESS FOR THE PREPARATION OF α-TOCOPHEROL

BACKGROUND OF THE INVENTION a) Field of the Invention

This invention relates to a novel process for the preparation of a α-tocopherol useful as an antisterile vitamin, hypolipidemic, blood flow increasing agent, oxygen radial scavenger, anticytosenility agent, antioxidant and the like.

b) Description of the Related Art

α-Tocopherol has heretofore been prepared by condensing trimethylhydroquinone represented by the following formula (I):

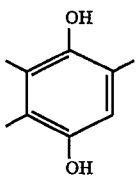

with any one of phytols represented by the following formulae:

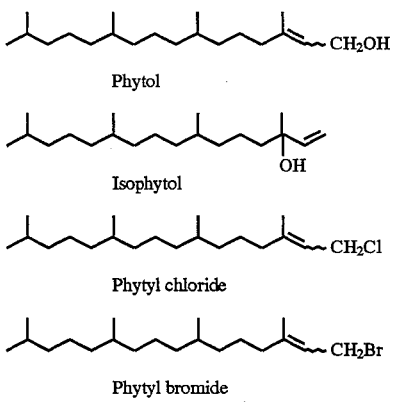

in accordance with the Friedel-Crafts reaction,

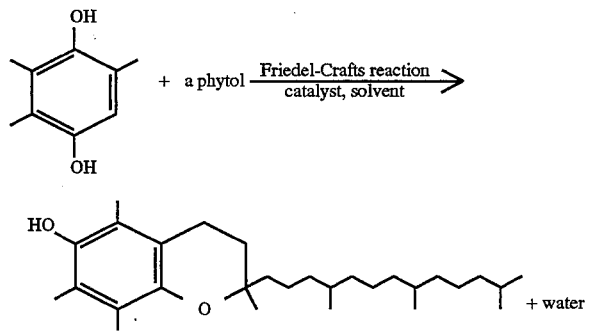

In this reaction, it is preferred to use a solvent, for example, to control the reaction heat and/or to lower the viscosity of the reaction mixture. Specifically, ethyl acetate, hexane, benzene, toluene, methylene chloride or the like is used. Among these, ethyl acetate is commonly used.

This common use of ethyl acetate as solvent for preparing α-tocopherol can be attributed to its appropriate solubility for trimethylhydroquinone (I) and also to its abundant availability at low cost in industry.

Ethyl acetate, however, is accompanied by problems such that upon washing a reaction mixture subsequent to the reaction, ethyl acetate is caused to transfer at a high rate into a water layer, its recovery rate is low, and treatment of waste water from the washing is difficult.

Further, ethyl acetate is extremely prone to hydrolysis under conditions other than neutral conditions, especially under basic conditions. It also tends to undergo a transesterification. Due to these properties, there is a further problem that when ethyl acetate is employed in the preparation of α-tocopherol, by production of α-tocopheryl acetate is unavoidable.

As α-tocopherol and α-tocopheryl acetate have extremely close physicochemical properties, they cannot be separated and purified by any industrial purification method such as molecular distillation. Nevertheless, α-tocopherol is required to have an extremely high purity when employed as medicines, a base material for cosmetics, foods or the like. The preparation process of α-tocopherol, which makes use of ethyl acetate as a solvent, has therefore been difficult to meet the demand for such high-purity α-tocopherol.

On the other hand, use of a single kind of nonpolar Solvent such as hexane, benzene or toluene tends to produce static electricity upon its charging or its transfer through piping in a dry season such as winter, whereby inflammation and/or explosion hazards are involved.

As has been described above, the conventional preparation process of α-tocopherol, which uses ethyl acetate or a single kind of nonpolar solvent, is accompanied by many problems from the viewpoints of product purity, economy, waste treatment, safety and the like, resulting in the long standing desire for an excellent industrial solvent which can substitute for such conventional solvents.

SUMMARY OF THE INVENTION

With a view toward improving the above-described problems of the conventional solvents, the present inventors have proceeded with an extensive investigation. As a result, it has been found that use of a carbonate ester (IV), a lower fatty acid ester (V) or a mixed solvent of a nonpolar solvent (VI) and a lower alcohol having 1–5 carbon atoms (VII) or the lower fatty acid ester (V) as a solvent makes it possible to industrially prepare α-tocopherol while attaining the above goal. This finding has led to the completion of the present invention.

An object of the present invention is therefore to provide an industrially excellent process for the preparation of α-tocopherol which is useful an antisterile vitamin, hypolipidemic, blood flow increasing agent, oxygen radial scavenger, anticytosenility agent, antioxidant and the like.

Here, trimethylhydroquinone (I) useful in the practice of the present invention is 2,3,5-trimethyl-1,4-hydroquinone and is represented by the following formula:

On the other hand, the phytol derivative (II) is represented by the following formula:

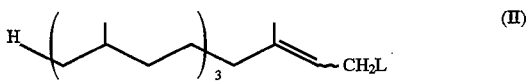

wherein L means a hydroxy group, a halogen atom or an acetoxy, methanesulfonyloxy, ethanesulfonyloxy, benzenesulfonyloxy or toluenesulfonyloxy group.

Specific examples of the phytol derivative (II) include, but are not limited to, the following compounds:

(1) Phytol,
(2) Phytyl chloride,
(3) phytyl bromide,
(4) Phytyl iodide,
(5) Phytyl acetate,
(6) Phytyl methanesulfonate,
(7) Phytyl ethanesulfonate,
(8) Phytyl benzenesulfonate, and
(9) Phytyl toluenesulfonate.

Next, the isophytol (III) is represented by the following formula:

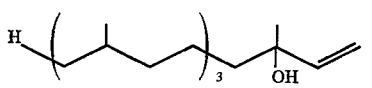

(III)

Further, specific examples of the carbonate ester (IV) include, but are not limited to, the following compounds:

(1) Dimethyl carbonate,
(2) Diethyl carbonate,
(3) Dipropyl carbonate,
(4) Methylethyl carbonate,
(5) Ethylene carbonate, and
(6) Propylene carbonate.

Among these, dimethyl carbonate, diethyl carbonate, methylethyl carbonate and propylene carbonate are more preferred.

In addition, the lower fatty acid ester (V) useful in the practice of the present invention is represented by the following formula:

$$R^1COOR^2 \quad (V)$$

wherein $R^1$ means a lower alkyl group having 1–4 carbon atoms and $R^2$ means a lower alkyl group having 1–5 carbon atoms with the proviso that methyl acetate and ethyl acetate are excluded. This means that neither methyl acetate nor ethyl acetate is used as the lower fatty acid ester (V) in the present invention. Specific examples of the lower fatty acid ester (V) include, but are not limited to, the following compounds:

(1) n-Propyl acetate,
(2) i-Propyl acetate,
(3) n-Butyl acetate,
(4) i-Butyl acetate,
(5) t-Butyl acetate,
(6) n-Amyl acetate,
(7) i-Amyl acetate [$CH_3COOCH_2CH_2CH(CH_3)_2$],
(8) sec-Amyl acetate [$CH_3COOCH(CH_3)CH_2CH_2CH_3$],
(9) t-Amyl acetate [$CH_3COOC(CH_3)_2CH_2CH_3$],
(10) 2,2-Dimethylpropyl acetate [$CH_3COOCH_2C(CH_3)_3$],
(11) 2-Methylbutyl acetate [$CH_3COOCH_2CH(CH_3)CH_2CH_3$],
(12) Methyl propionate,
(13) n-Butyl propionate,
(14) Ethyl butyrate,
(15) i-Propyl butyrate,
(16) Methyl isobutyrate,
(17) Ethyl isobutyrate,
(18) i-Butyl isobutyrate,
(19) Methyl valerate,
(20) Ethyl valerate,
(21) Methyl isovalerate,
(22) Ethyl isovalerate,
(23) Methyl pivalate, and
(24) Ethyl pivalate.

Of these, more preferred are n-propyl acetate, i-propyl acetate, n-butyl acetate, i-butyl acetate, n-butyl propionate, ethyl butyrate, i-propyl butyrate, methyl isobutyrate, ethyl isobutyrate, methyl Valerate, ethyl isovalerate and ethyl pivalate.

On the other hand, specific examples of the nonpolar solvent (VI) include, but are not limited to, the following compounds:

(1) Pentane,
(2) Hexane,
(3) Heptane,
(4) Octane,
(5) Ligroin,
(6) Petroleum ether,
(7) Cylohexane,
(8) Benzene,
(9) Toluene, and
(10) Xylene.

Of these, more preferred are hexane, heptane, ligroin, cyclohexane, toluene and xylene.

Finally, specific examples of the lower alcohol having 1–5 carbon atoms (VII) include, but are not limited to, the following compounds:

(1) Methanol,
(2) Ethanol,
(3) n-Propanol,
(4) i-Propanol,
(5) n-Butanol,
(6) i-Butanol,
(7) t-Butanol,
(8) n-Amyl alcohol (also called "1-pentanol"),
(9) 2-Pentanol (also called "1-methyl-1-butanol"),
(10) 3-Pentanol (also called "1-ethyl-1-propanol"),
(11) i-Amyl alcohol (also called "3-methyl-1-butanol),
(12) t-Amyl alcohol (also called "1,1-dimethyl-1-propanol"),
(13) 2,2-Dimethyl-1-propanol,
(14) 1,2-Dimethyl-1-propanol,
(15) 2-Methyl-1-butanol, and
(16) 3-Methyl-2-butanol.

Of these, more preferred are n-propanol, i-propanol, n-butanol, i-butanol, t-butanol, n-amyl alcohol, 2-pentanol, 3-pentanol, i-amyl alcohol and t-amyl alcohol.

The preparation process according to the present invention will hereinafter be described in detail.

The process according to the present invention for the preparation of α-tocopherol features that in a condensation reaction between trimethylhydroquinone (I) and the phytol derivative (II) or isophytol (III), the reaction is conducted in the presence of the carbonate ester (IV), the lower fatty acid ester (V), or the mixed solvent of the nonpolar solvent (VI) and the lower alcohol having 1–5 carbon atoms (VII) or the lower fatty acid ester (V). Accordingly, one of the following solvents is employed (1) Carbonate ester (IV),
(2) Lower fatty acid ester (V),
(3) Mixed solvent of the nonpolar solvent (VI) and the lower alcohol having 1-5 carbon atoms (VII), and
(4) Mixed solvent of the nonpolar solvent (VI) and the lower fatty acid ester (V).

When the mixed solvent of the nonpolar solvent (VI) and the lower alcohol having 1-5 carbon atoms (VII) or the lower fatty acid ester (V) is used, no particular limitation is imposed on their mixing ratio. In general, However, the lower alcohol having 1-5 carbon atoms (VII) or the lower fatty acid ester (V) is added in a proportion of 0.1-50 vol. %, preferably 0.5-25 vol. %, more preferably 1-15 vol. % to the nonpolar solvent (VI), followed by mixing for use in the reaction.

Although no particular limitation is imposed on the amount of the solvent to be employed, the solvent is used generally in an amount of about 0.5-100 ml per gram of trimethylhydroquinone (I), with about 0.7-50 ml being preferred and about 1-20 ml more preferred. It is to be noted that the solvent can be used either singly or as a mixture with an additional solvent.

When an additional solvent is used, no particular limitation is imposed thereon insofar as it is inert to trimethylhydroquinone (I), the phytol derivative (II), isophytol (III) or a catalyst. Specific examples of such an additional solvent include the following solvents:

Benzene, toluene, xylene, nitrobenzene, chlorobenzene, dichlorobenzene, nitromethane, tetrahydrofuran, 1,2-dimethoxyethane, ethyl ether, isopropyl ether, butyl ether, methyl acetate, ethyl acetate, propyl acetate, methyl propionate, ethyl propionate, methyl butyrate, ethyl butyrate, acetone, 2-butanone (methyl ethyl ketone), 3-pentanone (diethyl ketone), 3-hexanone (ethyl propyl ketone), 4-heptanone (dipropyl ketone), 2,4-dimethyl-3-pentanone (diisopropyl ketone), propyl alcohol, butyl alcohol, pentanol, t-amyl alcohol, hexane, octane, decane, decalin, cyclohexane, methylene chloride, chloroform, carbon tetrachloride, 1,2-dichloroethane, 1,1,1-trichloroethane, 1,1,2-trichloroethane, trichlene, 1,1,1,2-tetrachloroethane, 1,1,2,2-tetrachloroethane, 1-chloropropane, 2-chloropropane, 1,1-dichloropropane, 1,2-dichloropropane, 1,3-dichloropropane, 2,2-dichloropropane, 1,4-dioxane, and 1,3-dioxolane.

The preparation process of the present invention can be conducted in a manner known per se in the art with respect to the Friedel-Crafts reaction. In general, trimethylhydroquinone (I), a catalyst and a solvent are mixed, to which the phytol derivative (II) or isophytol (III) is added in an amount of about 0.9-1.1 equivalents based on the trimethylhydroquinone (I). Although it is preferred to conduct the reaction under a stream of an inert gas such as nitrogen or argon, the reaction can also be conducted without such an inert gas. No limitation is therefore imposed on the environment for the reaction.

The term "catalyst" as used herein means a catalyst commonly employed in the Friedel-Crafts reaction, such as a mineral acid, Lewis acid, acidic ionexchange resin or a triflate, nitrate or sulfate of scandium, yttrium or a lanthanoid element. Although no particular limitation is imposed on the amount of the catalyst to be used, the catalyst is used generally in a proportion of about 0.001-1.5 equivalents based on trimethylhydroquinone (I), with about 0.005-1.0 equivalent being preferred and about 0.01-0.5 equivalent more preferred. Such catalyst can be used either singly or in some combination. In addition, a cocatalyst such as hydrochloric acid, sulfuric acid, phosphoric acid or p-toluenesulfonic acid can also be added.

The reaction in the present invention can be conducted at a temperature in a range of from ice cooled temperature to the reflux temperature of the solvent. At room temperature, the reaction is generally brought to completion in 1-12 hours or so. The reaction time can be shortened by conducting reaction under heat of about 100° C. or under reflux. Depending on the catalyst, it is also possible to shorten the reaction time further by azeotropically eliminating water.

α-Tocopherol so prepared can be purified by a method known per se in the art, such as silica gel column chromatography, HPLC or molecular distillation.

To specifically describe the present invention, Comparative Examples and Examples will be described next. Needless to say, the present invention is by no means limited to or by them.

Comparative Example 1

Synthesis of α-tocopherol (solvent: ethyl acetate)

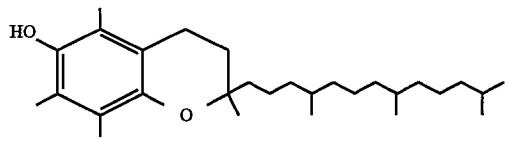

To a mixture consisting of 23.3 g (0.153 mol) of 2,3,5-trimethylhydroquinone, 17.5 g (0.128 mol) of zinc chloride, 54 ml of ethyl acetate and 2.5 g of concentrated hydrochloric acid, 46.1 g (0.153 mol) of isophytol (purity: 98.3%) were added dropwise under stirring at 25°-30° C. over 3 hours. At the same temperature, the reaction mixture was stirred for additional 2 hours. After the reaction mixture was washed with 10 ml of water, the solvent was distilled off. Toluene (100 ml) was added to the residue to dissolve the same. The resulting solution was washed successively with water, alkaline water and a saturated aqueous solution of NaCl, dried over magnesium sulfate and then concentrated under reduced pressure, whereby 66.0 g of the title compound were obtained as a brown oil (yield: 95.2%, GLC purity: 95.1%, αtocopheryl acetate content: 2.0%, ethyl acetate recovery rate: 50%).

Comparative Examples 2–8

Synthesis of α-tocopherol (conventional solvents).

The procedures of Comparative Example 1 were repeated by changing the solvent. The following results were obtained.

TABLE 1

Results of Synthesis of α-Tocopherol by Conventional Solvents

| Comp. Ex. | Solvent | Yield (g) | Yield (%) | GLC purity (%) |
|---|---|---|---|---|
| 2 | Toluene | 64.2 | 91.6 | 94.0 |
| 3 | Heptane | 64.5 | 93.3 | 95.3 |
| 4 | Cyclohexane | 63.0 | 90.5 | 94.7 |
| 5 | Diethyl ketone | 60.4 | 86.5 | 94.4 |
| 6 | Methyl isobutyl ketone | 67.4 | 97.7 | 95.6 |
| 7 | Ligroin | 66.3 | 83.1 | 82.6 |
| 8 | n-Butanol | 66.2 | 56.2 | 55.9 |

EXAMPLE 1

Synthesis of α-tocopherol (solvent: isobutyl acetate)

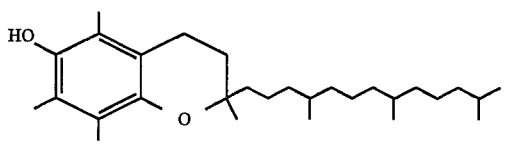

To a mixture consisting of 23.3 g (0.153 mol) of 2,3,5-trimethylhydroquinone, 17.5 g (0.128 mol) of zinc chloride, 50 ml of isobutyl acetate and 2.5 g of concentrated hydrochloric acid, 46.1 g (0.153 mol) of isophytol (purity: 98.3%) were added dropwise under stirring at 30°–40° C. over 3 hours. At the same temperature, the reaction mixture was stirred for additional 2 hours. After the reaction mixture was washed with 10 ml of water, the solvent was distilled off. Toluene (100 ml) was added to the residue to dissolve the same. The resulting solution was washed successively with water, alkaline water and a saturated aqueous solution of NaCl dried over magnesium sulfate and then concentrated under reduced pressure, whereby 67.0 g of the title compound were obtained as a brown oil (yield: 98.6%, GLC purity: 98.6%, α-tocopheryl acetate content: 0.2%, isobutyl acetate recovery rate: 92%).

EXAMPLE 2

Synthesis of α-tocopherol (solvent: isobutyl acetate)

To a mixture consisting of 69.9 g (0.460 mol) of 2,3,5-trimethylhydroquinone, 52.5 g (0.386 mol) of zinc chloride, 150 ml of isobutyl acetate and 7.5 g of concentrated hydrochloric acid, 138.3 g (0.459 mol) of isophytol (purity: 98.3%) were added dropwise under stirring at 30°–40° C. over 3 hours. At the same temperature, the reaction mixture was stirred for additional 2 hours. After the reaction mixture was washed with 30 ml of water, the solvent was distilled off. Toluene (300 ml) was added to the residue to dissolve the same. The resulting solution was washed successively with water, alkaline water and a saturated aqueous solution of NaCl dried over magnesium sulfate and then concentrated under reduced pressure, whereby 202.0 g of the title compound were obtained as a brown oil (yield: 99.6%, GLC purity: 97.5%).

EXAMPLE 3–5

Synthesis of α-tocopherol (solvents: acetate esters)

The procedures of Example 1 were repeated by changing the solvent. The following results were obtained.

TABLE 2

Results of Synthesis of α-Tocopherol by Acetate Ester Solvents

| Ex. | Solvent | Yield (g) | Yield (%) | GLC purity (%) |
|---|---|---|---|---|
| 3 | n-Propyl acetate | 67.0 | 98.3 | 96.7 |
| 4 | i-Propyl acetate | 66.8 | 97.9 | 96.6 |
| 5 | n-Butyl acetate | 66.9 | 98.5 | 97.0 |

EXAMPLE 6–13

Synthesis of α-tocopherol (solvents: other lower fatty acid esters)

The procedures of Example 1 were repeated by changing the solvent. The following results were obtained.

TABLE 3

Results of Synthesis of α-Tocopherol by Lower Fatty Acid Esters

| Ex. | Solvent | Yield (g) | Yield (%) | GLC purity (%) |
|---|---|---|---|---|
| 6 | n-Butyl propionate | 67.0 | 98.6 | 97.0 |
| 7 | Ethyl butyrate | 66.8 | 98.5 | 97.2 |
| 8 | i-Propyl butyrate | 66.5 | 98.0 | 97.1 |
| 9 | Methyl isobutyrate | 66.6 | 98.4 | 97.4 |
| 10 | Ethyl isobutyrate | 66.5 | 98.0 | 97.1 |
| 11 | Methyl valerate | 66.3 | 97.4 | 96.8 |
| 12 | Ethyl isovalerate | 66.2 | 97.3 | 96.9 |
| 13 | Ethyl pivalate | 66.0 | 96.8 | 96.7 |

EXAMPLE 14

Synthesis of α-tocopherol (solvent: diethyl carbonate)

To a mixture consisting of 23.3 g (0.153 mol) of 2,3,5-trimethylhydroquinone, 17.5 g (0.128 mol) of zinc chloride, 50 ml of diethyl carbonate and 2.5 g of concentrated hydrochloric acid, 46.1 g (0.153 mol) of isophytol (purity: 98.3%) were added dropwise under stirring at 30°–40° C. over 3 hours. At the same temperature, the reaction mixture was stirred for additional 2 hours. After the reaction mixture was washed with 10 ml of water, the solvent was distilled off. Toluene (100 ml) was added to the residue to dissolve the same. The resulting solution was washed successively with water, alkaline water and a saturated aqueous solution of NaCl dried over magnesium sulfate and then concentrated under reduced pressure, whereby 67.0 g of the title compound were obtained as a brown oil (yield: 98.9%, GLC purity: 97.3%).

EXAMPLE 15

Synthesis of α-tocopherol (solvent: diethyl carbonate)

To a mixture consisting of 69.9 g (0.460 mol) of 2,3,5-trimethylhydroquinone, 52.5 g (0.386 mol) of zinc chloride, 150 ml of diethyl carbonate and 7.5 g of concentrated hydrochloric acid, 138.3 g (0.459 mol) of isophytol (purity: 98.3%) were added dropwise under stirring at 30°–40° C. over 3 hours. At the same temperature, the reaction mixture was stirred for additional 2 hours. After the reaction mixture was washed with 30 ml of water, the solvent was distilled off. Toluene (300 ml) was added to the residue to dissolve the same. The resulting solution was washed successively with water, alkaline water and a saturated aqueous solution of NaCl dried over magnesium sulfate and then concentrated under reduced pressure, whereby 201.2 g of the title compound were obtained as a brown oil (yield: 99.2%, GLC purity: 97.5%).

EXAMPLE 16–19

Synthesis of α-tocopherol (solvents: carbonate esters)

The procedures of Example 14 were repeated by changing the solvent. The following results were obtained.

TABLE 4

Results of Synthesis of α-Tocopherol by Carbonate Ester Solvents

| Ex. | Solvent | Yield (g) | Yield (%) | GLC purity (%) |
|---|---|---|---|---|
| 16 | Dimethyl carbonate | 66.5 | 97.7 | 96.8 |
| 17 | Ethylene carbonate | 67.0 | 94.0 | 92.5 |
| 18 | Propylene carbonate | 66.6 | 97.2 | 96.2 |
| 19 | Methyl ethyl carbonate | 66.0 | 97.2 | 97.0 |

EXAMPLE 20

Synthesis of α-tocopherol (solvent: hexane/n-butanol mixed solvent system)

To a mixture consisting of 23.3 g (0.153 mol) of 2,3,5-trimethylhydroquinone, 17.5 g (0.128 mol) of zinc chloride, 47.5 ml of hexane, 2.5 ml of n-butanol and 2.5 g of concentrated hydrochloric acid, 46.1 g (0.153 mol) of isophytol (purity: 98.3%) were added dropwise under stirring at 30°–40° C. over 3 hours. At the same temperature, the reaction mixture was stirred for additional 2 hours. After the reaction mixture was washed with 10 ml of water, the solvents were distilled off. Toluene (100 ml) was added to the residue to dissolve the same. The resulting solution was washed successively with water, alkaline water and a saturated aqueous solution of NaCl, dried over magnesium sulfate and then concentrated under reduced pressure, whereby 69.0 g of the title compound were obtained as a brown oil (yield: 95.9%, GLC purity: 97.2%).

EXAMPLE 21

Synthesis of α-tocopherol (solvent: hexane/n-butanol mixed solvent system)

To a mixture consisting of 69.9 g (0.260 mol) of 2,3,5-trimethylhydroquinone, 52.5 g (0.386 mol) of zinc chloride, 142.5 ml of hexane, 7.5 ml of n-butanol and 7.5 g of concentrated hydrochloric acid, 138.3 g (0.459 mol) of isophytol (purity: 98.3%) were added dropwise under stirring at 30°–40° C. over 3 hours. At the same temperature, the reaction mixture was stirred for additional 2 hours. After the reaction mixture was washed with 30 ml of water, the solvents were distilled off. Toluene (300 ml) was added to the residue to dissolve the same. The resulting solution was washed successively with water, alkaline water and a saturated aqueous solution of NaCl dried over magnesium sulfate and then concentrated under reduced pressure, whereby 200 g of the title compound were obtained as a brown oil (yield: 98.1%, GLC purity: 97.0%).

EXAMPLE 22–29

Synthesis of α-tocopherol (solvents: mixed solvent systems)

The procedures of Example 21 were repeated by changing the solvents. The following results were obtained.

TABLE 5

Results of Synthesis of α-Tocopherol by Mixed Solvent Systems

| Ex. | Solvent | Yield (g) | Yield (%) | GLC purity (%) |
|---|---|---|---|---|
| 22 | Hexane + 5% isobutyl acetate | 65.4 | 96.0 | 96.7 |
| 23 | Toluene + 5% n-propanol | 66.2 | 95.5 | 95.1 |
| 24 | Heptane + 5% n-butanol | 64.0 | 94.1 | 96.9 |
| 25 | Cyclohexane + 5% n-butanol | 65.5 | 95.8 | 96.4 |
| 26 | Toluene + 5% n-butanol | 64.5 | 92.8 | 94.8 |
| 27 | Ligroin + 5% n-butanol | 66.5 | 95.8 | 94.9 |
| 28 | Toluene + 5% n-pentanol | 67.3 | 94.5 | 92.5 |
| 29 | Toluene + 5% | 69.4 | 96.6 | 91.7 |

What is claimed is:

1. A process for the preparation of α-tocopherol by a condensation reaction between trimethylhydroquinone represented by the following formula (I):

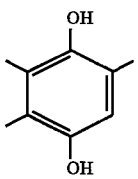

and a phytol derivative represented by the following formula (II):

wherein L means a hydroxy group, a halogen atom an acetoxy, methanesulfonyloxy, ethanesulfonyloxy, benzenesulfonyloxy or toluenesulfonyloxy group, or isophytol represented by the following formula (III):

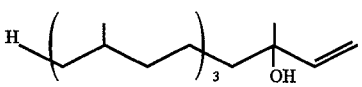

which comprises conducting the condensation reaction in the presence of a carbonate ester (IV) as a solvent and $ZnCl_2$ plus concentrated HCl as a catalyst.

2. The process according to claim 1, wherein the carbonate ester (IV) is one or more of the solvents selected from the group consisting of dimethyl carbonate, diethyl carbonate, dipropyl carbonate, methylethyl carbonate, ethylene carbonate and propylene carbonate.

* * * * *